United States Patent [19]

Sterzycki et al.

[11] Patent Number: 5,126,506
[45] Date of Patent: Jun. 30, 1992

[54] 2',3'-DIDEOXY-2'-FLUORONUCLEOSIDES

[75] Inventors: Roman Z. Sterzycki, Madison; Muzammil M. Mansuri; John C. Martin, both of Cheshire, all of Conn.

[73] Assignee: Bristol-Myers Company, New York, N.Y.

[21] Appl. No.: 581,941

[22] Filed: Sep. 13, 1990

Related U.S. Application Data

[62] Division of Ser. No. 378,331, Jul. 11, 1989, Pat. No. 4,973,677, which is a division of Ser. No. 120,051, Nov. 12, 1987, Pat. No. 4,908,440.

[51] Int. Cl.⁵ .............................................. C07H 17/00
[52] U.S. Cl. .......................................... 536/23; 536/24
[58] Field of Search .................................... 536/23, 24

[56] References Cited

PUBLICATIONS

Kinney-Thomas, et al. Biochem. Pharm 36: 311–316, 1987.
Mitsuya, et al. P.N.A.S. U.S.A. 83: 1911–1915, 1986.
Chem Eng. News, Oct. 23, 1987, pp. 44, 45 & 48.
Baba et al. Biochem & Biophys. Res. Comm. 142: 128–134, 1987.

Primary Examiner—John W. Rollins
Attorney, Agent, or Firm—Aldo A. Algieri

[57] ABSTRACT

There are disclosed novel 2',3'-dideoxy-2'-fluoronucleosides and 2'-3'-dideoxy-2',3'-didehydro-2'-fluoronucleosides and processes for their preparation. The compounds so produced exhibit therapeutically useful antiviral and, more particularly, anti-HIV effects.

4 Claims, No Drawings

2',3'-DIDEOXY-2'-FLUORONUCLEOSIDES

CROSS REFERENCE

This application is a divisional of U.S. Ser. No. 378,331, filed Jul. 11, 1989, now U.S. Pat. No. 4,973,677 which is a divisional of U.S. Ser. No. 120,051, filed Nov. 12, 1987, U.S. Pat. No. 4,908,440.

BACKGROUND OF THE INVENTION

1. Field of the Invention

This invention relates to 2',3'-dideoxy-2'-fluoronucleosides and 2',3'-dideoxy-2',3-didehydro-2'-fluoronucleosides, their preparation, and their use in HIV infection.

2. Background - Related References

Marquez et al., *Biochem. Pharmacol.*, 36 (17), 2719–2722 (1987) disclose two 2'-F-substituted dideoxynucleoside derivatives of dideoxyadenosine (ddA; compound (A)) which constitute acid stable, active anti-HIV agents. These two compounds are shown below and designated compound B [6-amino-($\beta$'D-2',3'-dideoxy-2'-fluororibofuranosyl)-9-H-purine; 2'-F-ddA] and compound C [6-amino-9-($\bar{\beta}$-D-2',3'-dideoxy-2'-fluoroarabinofuranosyl)-H-purine; 2'-F-ara-ddA].

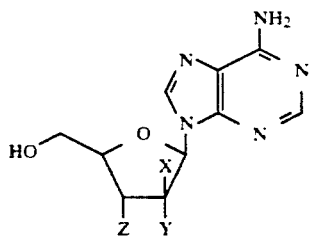

A. X = H; Y = H; Z = H
B. X = H; Y = F; Z = H
C. X = F; Y = H; Z = H
D. X = OH; Y = H; Z = H
E. X = F; Y = H; Z = OH

Compound B was obtained from 3'-deoxy-ara-A (compound D) in four steps which involved protection of the 5'-hydroxyl group with dimethoxytrityl chloride, activation of the 2'-hydroxyl group via formation of the corresponding triflate, inversion of configuration at the 2'-position by an $SN_2$ displacement using tetra-n-butylammonium fluoride, and removal of the dimethoxytrityl protective group using dichloracetic acid.

Compound C was prepared by condensing 6-chloropurine with 3-O-acetyl-5-O-benzyl-2-deoxy-2-fluoro-D-arabinofuranosyl bromide, separating the expected four isomers and characterizing the correct 6-chloro isomer, and subjecting the correct isomer to ammonolysis with concentrated methanolic ammonia to give Compound E, 6-amino-9-($\beta$-D-2'deoxy-2'-fluoroarabinofuranosyl)-9$\underline{H}$-purine (2'F-ara-dA; compound E). Selective protection of the 5'-hydroxyl function of Compound E with t-butyldimethylsilyl chloride gave a product that permitted the 2-step reduction of the 3'-hydroxy group. Treatment with phenyl chlorothionocarbonate, followed by reduction of the intermediate 3'-O-phenoxythiocarbonyl derivative with tri-n-butyl tin hydride, produced the desired 2',3'-dideoxynucleoside. Removal of the 5'-blocking group with tetra-n-butyl ammonium fluoride gave 2'-F-ara-ddA (compound C).

The results of biological testing showed that Compound C having stereochemistry of fluorine at the 2'-position in the $\beta$ ("up") configuration provided a compound about as active and potent as AZT or ddA against HIV. Compound B having fluoride at the 2'-position in the $\alpha$ ("down") configuration gave dramatically different activity, being protective against HIV to 13% of that protection seen with ddA and was more toxic than ddA.

U.S. Ser. No. 028817 filed Mar. 20, 1987, cross-referenced above, discloses a process for producing 2',3'-dideoxynucleosides represented by the formula.

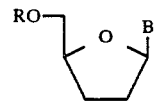

The process for producing two representative dideoxynucleoside according to U.S. Ser. No. 028817 is outlined in Scheme I below.

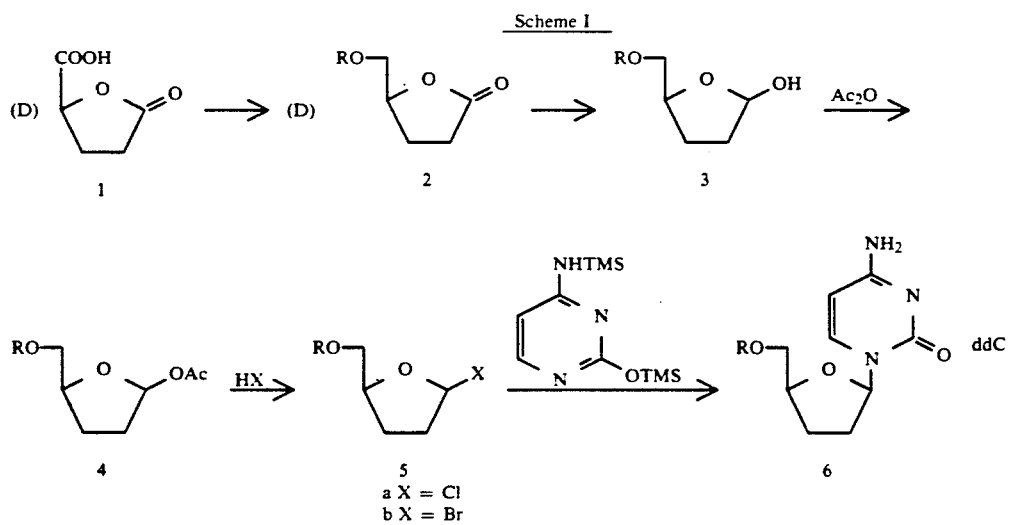

-continued
Scheme I

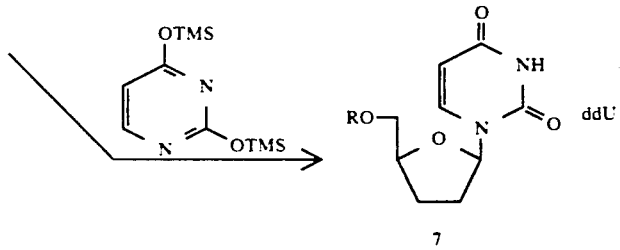

Brundidge et al., U.S. Pat. No. 4,625,020, discloses a process for producing 1-halo-2-deoxy-2-fluoroarabinofuranoside derivatives (Compound of Formula F), bearing protective ester groups, from 1,3,5-tri-O-acyl-ribofuranose. The 1-halo derivatives are intermediates in the synthesis of therapeutically active nucleosidic compounds (compound of Formula G).

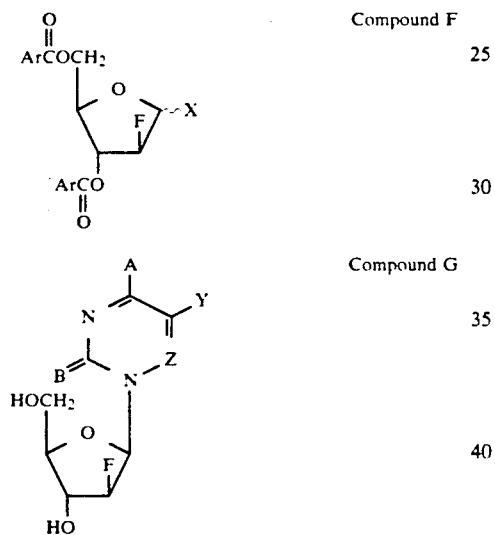

Compound F

Compound G

Lopez et al., EP Patent App. Publication No. 0,010,205 discloses 5-substituted 1-(2'-deoxy-2'-substituted-beta-D-arabinofuranosyl)pyrimidine nucleosides wherein the 2'-substituent, X, is halogen, alkylsulfonyl or arylsulfonyl (compound of Formula H).

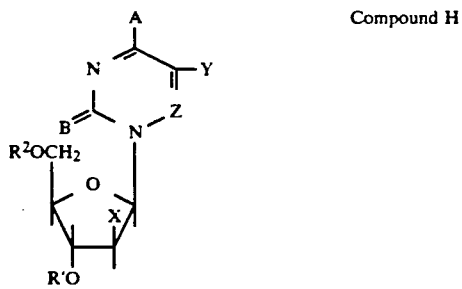

Compound H

SUMMARY OF THE INVENTION

This invention comprises novel 2',3'-dideoxy-2'-fluoronucleosides and 2'-3'-dideoxy-2',3'--didehydro-2'-fluoronucleosides and processes for their preparation. The compounds exhibit therapeutically useful antiviral effects and are useful as anti-human immunodeficiency virus (anti-HIV) infection agents.

DETAILED DESCRIPTION OF THE INVENTION

In one aspect, this invention is a compound having the formula

Formula I wherein:
(a) B is a member selected from the group of bases consisting of purine (except adenine), aza-purine, deaza-purine, pyrimidine, aza-pyrimidine, deaza-pyrimidine, and triazole ring bases; and (b) R is selected from hyrodgen (H) and a member of the group of substituents consisting of azido ($N_3$), cyano (CN), cyanamido (NHCN), halo (F, Cl, Br), amino ($NH_2$), monoalkylamino (NHR'), dialkylamino ($NR_2'$), alkylthio (SR'), sulfoxide (S(O)R') and sulfonyl ($S(O)_2R'$) groups wherein R' is selected from $C_1$-$C_3$ alkyl, phenyl and tolyl groups.

In another aspect, this invention is a compound having the formula

Formula II wherein:
(a) B is a member selected from the group of bases consisting of purine (except adenine), aza-purine, deaza-purine, pyrimidine, aza-pyrimidine, deaza-pyrimidine, and triazole ring bases; and (b) R is selected from hydrogen (H) and a member of the group of substituents consisting of azido ($N_3$), cyano (CN), cyanamido (NHCN), halo (F, Cl, Br), amino ($NH_2$), monoalkylamino (NHR'), dialkylamino ($NR_2'$), alkylthio (SR'), sulfoxide (S(O)R') and sulfonyl ($S(O)_2R'$) groups wherein R' is selected from $C_1$-$C_3$ alkyl, phenyl and tolyl groups.

In yet another aspect, this invention is a process for producing a compound according to Formula I comprising the steps of:

(a) reacting a 2'-deoxy-2'fluoroarabino-nucleoside with a hydroxy-protecting group reagent to selectively protect the 4'-hydroxymethyl group;

(b) subjecting the intermediate from step (a) to reductive deoxygenation to convert the 3'-hydroxy group in the intermediate from step (a) to a 3'-hydrogen group; and (c) deprotecting the 4'-hydroxymethyl group.

In still another aspect, this invention is a process for producing a compound according to Formula II comprising the steps of:

(a) reacting a 2'-deoxy-2'-fluoroarabino-nucleoside with a hydroxy-protecting group reagent to selectively protect the 4'-hydroxymethyl group;

(b) subjecting the intermediate from step (a) to reaction conditions effective to convert the 3'-hydroxy group to 3'-O-leaving group substituent;

(c) subjecting the intermediate from step (b) to elimination reaction conditions to form a double bond between the 2'- and 3'-positions of the 5-membered ring system; and (d) deprotecting the 4'-hydroxymethyl group.

In yet another aspect, this invention is a process for producing a compound according to Formula I comprising the steps of:

(a) reacting a 2'-deoxy-2'-fluoroarabino-nucleoside with a hydroxy-protecting group reagent to selectively protect the 4'-hydroxymethyl group;

(b) subjecting the intermediate from step (a) to reaction conditions effective to convert the 3'-hydroxy group to 3'-O-leaving group substituent; (c) subjecting the intermediate from step (c) to elimination reaction conditions to form a double bond between the 2'- and 3'-positions of the 5-membered ring system;

(d) deprotecting the 4'-hydroxymethyl group; and (e) subjecting the intermediate from step (d) to reducing conditions effective to reduce the double bond connecting the 2' and 3' carbon atoms of the 5-membered ring system.

In still another aspect, this invention is a process for producing a compound according to Formula I wherein B is derived from a member of the group of bases consisting of uracil, thymine, cytosine, and guanine and wherein R is a member of said group of above-mentioned substituents comprising the steps of:

(a) subjecting 2'-deoxy-2'-fluoroarabinonucleoside having a hydroxy protecting group at the 5'-position and a 3'-O-leaving group to conditions effective to form a 3',2-anhydro bond; and (b) reacting the intermediate from step (a) with a nucleophile effective to disrupt the 3',2-anhydro bond and to introduce the 3'-substituent.

In yet another aspect, this invention is a pharmaceutical composition comprising an antiviral effective amount of the compound according to one of Formulas I and II and a pharmaceutically acceptable carrier.

In still another aspect, this invention is a method of treating an animal to eliminate or reduce the infection with the human immunodeficiency virus (HIV) by administering to said animal an anti-human immunodeficiency virus effective amount of a compound according to one of Formulas I and II.

As is mentioned above, the base component B is derived from a member selected from the group of bases consisting of purine (except adenine), aza-purine, deazapurine, pyrimidine, aza-pyrimidine, deaza-pyrimidine, and triazole ring bases. Preferably, the base is selected from purine and pyrimidine bases. More preferably, the base is a pyrimidine base including one of the group of uracil, thymine and cytosine.

Suitable purine bases include those purine bases represented by the structural formula

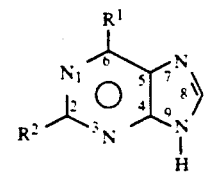

Formula III wherein $R^1$ and $R^2$ may be the same or different and are selected from hydrogen, hydroxy, halo (F, Cl, Br), amino, monoalkylamino, dialkylamino, alkoxy and cyano groups wherein the alkyl moiety is selected from $C_1$–$C_3$ alkyl groups, provided that $R^2$ is not H and $R^1$ is not $NH_2$.

Suitable pyrimidine bases include those pyrimidine bases represented by the structural formula

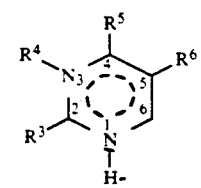

Formula IV wherein $R^3$ is selected from hydroxy, amino and sulfhydryl groups; $R^4$ is hydrogen; $R^5$ is selected from hydroxy and amino groups; and $R^6$ is selected from hydrogen, $C_1$–$C_3$ alkyl, $C_2$–$C_3$ alkenyl, $C_2$–$C_3$ haloalkenyl having from 1 to 5 halo groups as defined herein, $C_2$–$C_3$ alkynyl, alkoxy wherein the alkyl moiety has 1–3 carbon atoms, cyano and halo (F, Cl, Br and I).

When derived from purine bases, representative of B are the following:
2-aminopurin-9-yl
2,6-diaminopurin-9-yl
2-amino-6-hydroxypurin-9-yl (guanin-9-yl)
6-hydroxypurin-9-yl In addition to the above, the B component may be 2-halopurin-9-yl, 6-halopurin-9-yl, or 2,6-dihalopurin-9-yl, in which event the base component need not be activated, for example, completely silylated, in order to undergo the condensation or coupling reaction in step (e). When derived from pyrimidine bases, representative of B are the following:
2,6-dihydroxypyrimidin-1-yl
5-methyl-2,6-dihydroxypyrimidin-1-yl
5-ethyl-2,6-dihydroxypyrimidin-1-yl
2-hydroxy-6-aminopyrimidin-1-yl
5-vinyl-2,6-dihydroxypyrimidin-1-yl
5-halovinyl-2,6-dihydroxypyrimidin-1-yl
5-halomethyl-2,6-dihydroxypyrimidin-1-yl
5-haloethyl-2,6-dihydroxypyrimidin-1-yl The above-mentioned 5-methyl and 5-ethyl substituents are representative of 5-alkyl substituents and the 5-vinyl substituent is representative of 5-alkenyl substituents. Examples of halo-groups on the 5-halovinyl (or 5-haloalkenyl) group include 1 to 4 F, Cl, and Br groups.

The compounds having Formula I according to this invention are produced by the steps of:

(a) reacting a 2'-deoxy-2'fluoroarabino-nucleoside base with a hydroxy-protecting group reagent to selectively protect the 4'-hydroxymethyl group;

(b) subjecting the intermediate from step (a) to reductive deoxygenation to convert the 3'-hydroxy group in the intermediate from step (a) to a 3'-hydrogen group; and (c) deprotecting the 4'-hydroxymethyl group.

Alternatively, the compounds having Formula I according to this invention are produced by subjecting the compounds having Formula II according to this invention to reduction such as, for example, chemical reduction or catalytic hydrogenation or, when the Base is one of uracil, thymidine, cytosine and guanine and wherein R is a member of said group of above-mentioned substituents, by first forming a 3',2-anhydro intermediate and then reacting the intermediate with an nucleophile to introduce a 3'-substituent.

The compounds having Formula II according to this invention are produced by the steps of:

(a) reacting a 2'-deoxy-2'-fluoroarabino-nucleoside with a hydroxy-protecting group reagent to selectively protect the 4'-hydroxymethyl group;

(b) subjecting the intermediate from step (a) to reaction conditions effective to convert the 3'-hydroxy group to 3'-O-leaving group substituent;

(c) subjecting the intermediate from step (c) to elimination reaction conditions to form a double bond between the 2'- and 3'-positions of the 5-membered ring system; and (d) deprotecting the 4'-hydroxymethyl group.

SCHEMES II and III below illustrate typical, representative processes to produce compounds having Formulas I and II, respectively, according to this invention. The processes so illustrated were used in the actual examples which follow and may be used with alternative and equivalent reactants including starting materials, intermediates and reagents as will be apparent to those skilled in the art to which this invention pertains. As shown, the starting material is a 2'-deoxy-2'-fluoroarabino-nucleoside.

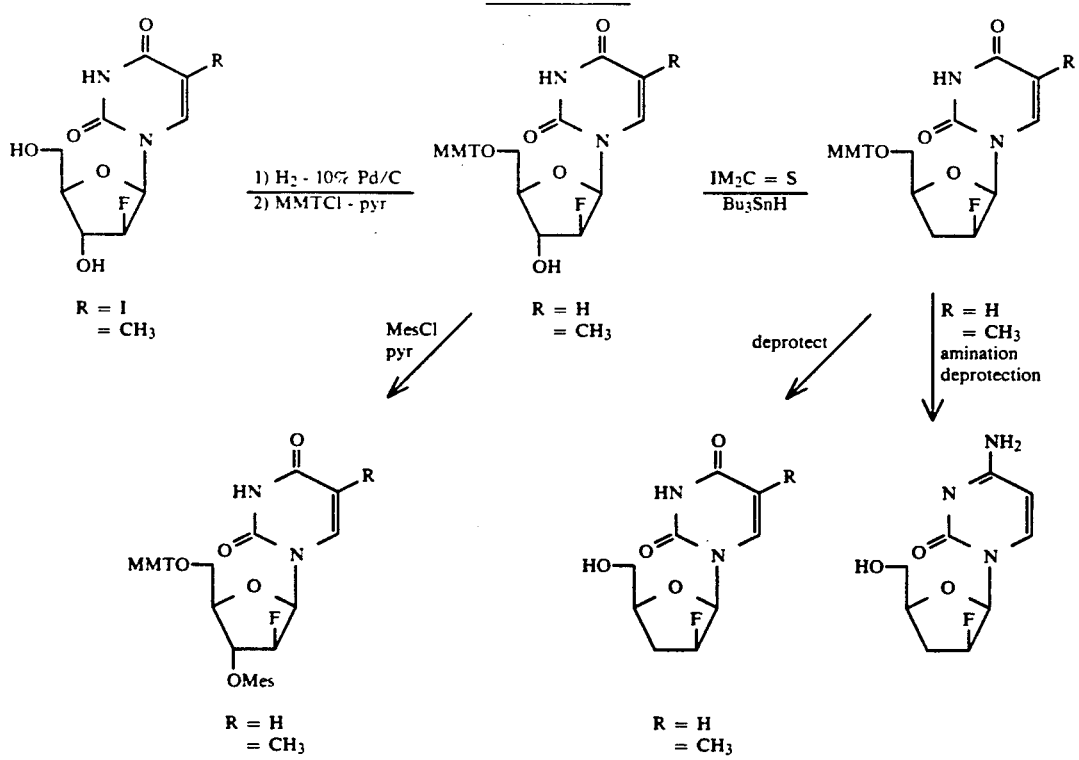

SCHEME II

SCHEME III

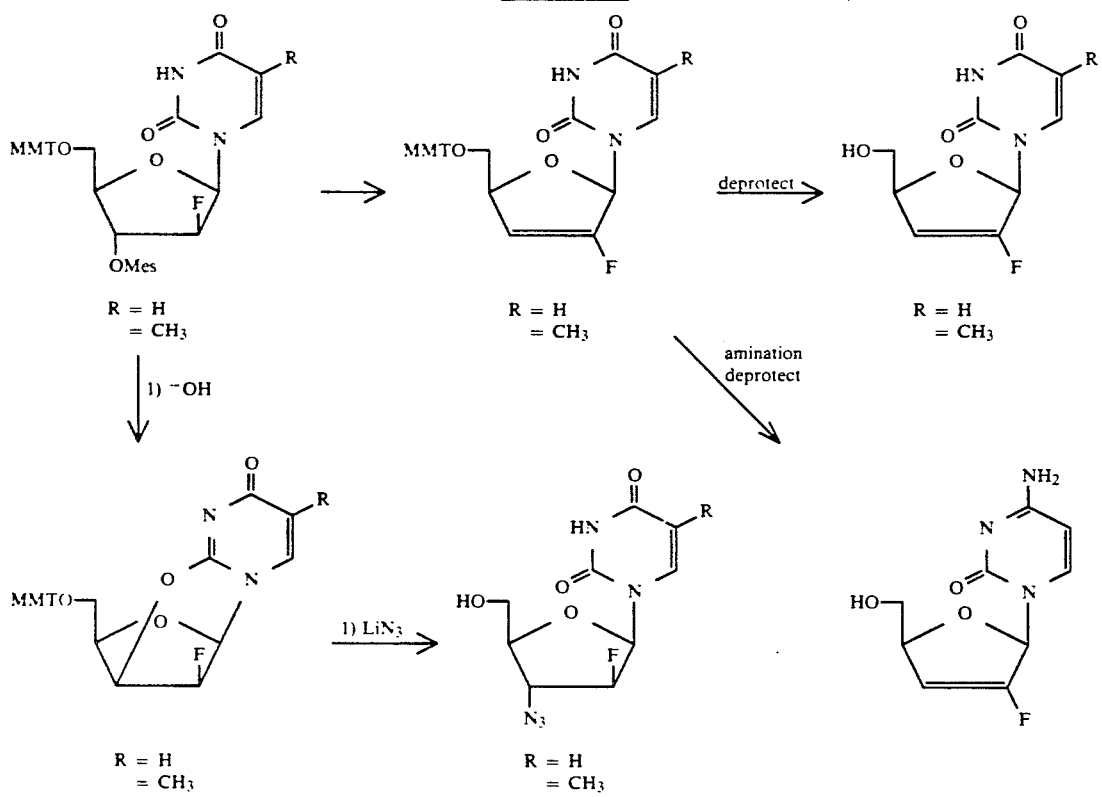

The above-mentioned starting compound can be obtained according to the procedures disclosed in the above-mentioned Brundidge et al. U.S. Pat. No. 4,625,020 or Lopez et al. EP Pat. App. Pub. 0,010,205. More particularly, the preparation of the starting material, 1-(2-deoxy-2-fluoro-2-D-arabinofuranosyl) 5-iodouracil (also known as 2'-deoxy-2'-fluoroarabino-5-iodo uridine) is described in Procedure 7 in the Brundidge et al. patent. When this compound is used as the starting material, it may conveniently be subjected to conventional catalytic dehalogenation to give 2'-deoxy-2'-fluoroarabino-uridine. Generally, the starting material useful to make the compounds according to this invention can be produced by reacting a 2-deoxy-2-fluoroarabinofuranosyl halide of the formula V

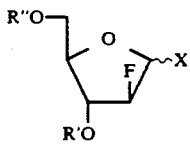

Formula V wherein R' and R", independently, are acyl, alkyl, aryl selected from conventional hydroxy group protecting groups, with a suitable base such as, for example, the preferred, activated-as-needed purine and pyrimidine bases having Formulas III and IV respectively,

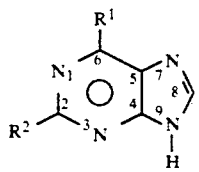

Formula III

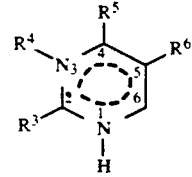

Formula IV wherein $R^1$, $R^2$, $R^3$, $R^4$, $R^5$, and $R^6$ are as defined above. Exemplary suitable procedures are described in U.S. Pat. No. 4,625,020 and EP Pat. App. Pub. 0,010,205.

SCHEMES II and III summarize typical, representative processes to produce the compounds according to this invention starting from 2'-deoxy-2'-fluoroarabino-thymidine. The given materials and the amounts thereof, the various reaction conditions employed in the several steps, and the means to isolate, purify, and characterize the several intermediates and final products will be readily apparent to those skilled in the art to which this invention pertains with this disclosure, including the actual examples which follow, in hand.

Thus, the processes according to this invention are useful for the preparation of a variety of 2'-fluoro-2', 3'-dideoxynucleosides and 2'-fluoro-2'3'-dideoxy-2',3'-didehydronucleosides, especially pyrimidine and purine nucleosides, having antiviral, antimetabolic, and antineoplastic activity as well as activity against human immunodeficiency viruses.

The following examples illustrate but a few representative embodiments of the compounds and processes according to this invention and are set forth to teach those skilled in the pertinent art how to practice this invention and are not to be construed as limiting in scope. All parts and percentages are by weight and temperatures are in degrees Celsius unless otherwise specified.

The anti-HIV data of representative compounds according to this invention are set forth in TABLE I. The compound numbers refer to the following actual examples illustrating preparation of the compounds according to this invention.

TABLE I

ANTI-HIV in vitro ACTIVITY OF SELECTED 2'-FLUORO-2', 3'-DIDEOXY-NUCLEOSIDES

| NUMBER | ABBR. NAME | M.P. deg. C. | ID50 (50% inhib. conc.) microM |
|---|---|---|---|
| 3 | 2'-FddU | 159–162 | not tested |
| 5 | 2'-FddC | 203–205 | 4 |
| 7 | 2'-Fddt | 162–164 | >100 |
| 11 | 2'-Fd4T | 129–131 | 10–100 |
| 16 | 2'-Fd4C | | 15–48 |
| 17 | 2'-FAZT | oil | >100 |

BIOLOGICAL ASSAYS

The assays were done in HTLV-1 transformed MT-2 cells infected with HIV virus. Inhibition of cytopathic effect CPE) was measured seven days after infection in comparison with control infected cells (Elaine Kinney-Thomas. (Bioch. Pharm., vol.36,pp 311–316, 1987).

2'-FLUORO-2',3'-DIDEOXYNUCLEOSIDES 1.
2'-Deoxy-2'-fluoroarabino-5'-monomethoxytrityl-uridine 2'-Deoxy-2'-fluoroarabino-uridine (8.9 g; 36.15 mM) dissolved in dry pyridine (120 ml) was heated for 8 hrs with monomethoxytrityl chloride (11.423; 37.00 mM) at 60°–80° C. and the volatiles were removed under vacuum. The residue was purified by column chromnatography on silica gel (20% EtOAc in CH$_2$Cl$_2$ to 40% EtOAc in CH$_2$Cl$_2$ followed by 10% EtOH in EtOAc) to give the title compound as an oil (7.4 g, 39.5%). 3.7 g of the starting material (s.m.) was recovered from EtOH/EtOAc washings. Yield: 67.57% based on consumed s.m..

2.
2',3'-Dideoxy-2'-fluoroarabino-5'-monomethoxytrityl-uridine

2'-Deoxy-2'-fluoroarabino-5'-monomethoxytrityl-uridine (7.2 g 13.88 mM) was stirred in dimethylformamide (DMF; 60 ml) for 2.7 hrs at 80°–90° C. with 1,1-thiocarbonyldiimidazole (3.46 g, 19.41 mM). The volatiles were removed in vacuo, and the oily residue (11 g) suspended in toluene and treated with azobisisobutyronitrile (AIBN, 200 mg), polymethylhydrosiloxane (40 ml) and bis-tributyltin oxide (40 ml). This mixture was heated under reflux for 6 hrs under argon and volatiles were removed in vacuo. The residue was treated with hexane (400 ml) and for 40 min. stirred at dry ice temp. The resulting supernatant was decanted, diluted with 100 ml of hexane and kept over dry ice overnight. The resulting supernatant was decanted and the combined residues were purified on a silica gel column (13% EtOAc in CH$_2$Cl$_2$ to 40% EtOAc in CH$_2$Cl$_2$). Yield 4.1 g(58.7%). PMR(360 MHz;CDCl$_3$): 9.23(bs,1,Nh), 7.53(dd,1.6 Hz, 8.2 Hz, 1, H-6), 7.45–7.21 m,12, aromatic), 6.83(m,2.aromatic). 6.05(dd, 18.0 Hz,3.2 Hz,1, H-1'), 5.58(d, 8.13 Hz, 1, H-5), 5.19(dm, 56.3 Hz,1,H-2'), 4.32(m, 1, H-4'), 3.78(s, 3, OCH$_3$), 3.32(m,2,H-5'), 2.47–2,34(m, 1, H-3a'), 2.28–2.03(m, 1, H-3').

3. 2',3'-Dideoxy-2'-fluoroarabino-uridine

2',3'-Dideoxy-2'-fluoroarabino-5'-monomethoxytrityl-uridine (1.7 g;3.38 mM) was dissoved in 80% aqueous acetic acid (80 ml) and stirred for 2.5 hrs at 55°–65° C. The volatiles were removed in vacuo and the residue was crystallized from MeOH-Et$_2$O-Hexane to give the pure product (500 mg). Additional material 110 mg was obtained from mother liquor through chromatography on a silica column(10% EtOH in EtOAc). Total yield: 610 mg(78.4%).M.p. 159°–162° C. For C$_9$H$_{11}$N$_2$O$_4$F Calc.: 47.0% C, 4.8% H, 12.2% N. Found: 46.6% C, 4.9% H, 12.0% N. PMR(360 MHz, d6 DMSO) 7.74(bd,8.1 Hz, 1, H-6), 5.97(dd, 16.8 Hz, 3.3 Hz, 1, H-1'), 5.62(dd, 8.1 Hz, 1.6 Hz, 1, H-5), 5.28(dm, 54.8 Hz, 1, H-2'), 5.01(t, 5.8 Hz, 1, OH), 4.095(m, 1, H-4'), 3.52(m, 2, H-5'), 2.54–2.38(m, 1, H-3a'), 2.2–1.98(m, 1, H-3b').

4.
2',3'-Dideoxy-2'-fluoroarabino-5'-monomethoxytrityl-cytidine

2',3'-Dideoxy-2'-fluoroarabino-5'-monomethoxytrityl-uridine (840 mg; 1.67 mM) was stirred in dry pyridine (5 ml) with p-chlorophenyl phosphodichloridate (1.23 g, 0.814 ml; 5.00 mM) and 1,2,4-triazole (693 mg, 10.0 mM) for 3 days. The mixture was partitioned between CH$_2$Cl$_2$ and H$_2$O and the organic extract was dried (Na$_2$SO$_4$) and evaporated. This resulting material was dissolved in 1,4-dioxane (15 ml) and stirred for 4 hrs with 27% aqueous ammonia (8 ml). The volatiles were removed in vacuo and remaining oil was purified on a silica gel column (3% EtOH/EtOAc–10% EtOH/EtOAc) to give the title product (590 mg, 70.4%). PMR(200 MHz, CDCl$_3$): 7.56(dd, 7.6 Hz, 3.0 Hz, 1, H-6), 7.50–7,20(m, 12, aromatic), 6.85(m, 2, aromatic), 6.08(dd, 18.2 Hz, 3.6 Hz, 1, H-1'), 5.61(d, 7.8 Hz, 1, H-5), 5.21(dm, 54.4 Hz, 1, H-2'), 4.35(m, 1, H-4'), 3.28(m, 2, H-5'), 2.62–2.06(m, 2, H-3').

5. 2',3'-Dideoxy-2'-fluoroarabino-cytidine

2',3'-Dideoxy-2'-fluoroarabino-5'-monomethoxytrityl-cytidine (420 mg; 0.837 mM) was stirred for 3 hrs. in 80% aqueous acetic acid (15 ml) at 60° C. The volatiles were removed in vacuo and the residue filtered through a short silica gel column (5% EtOH/EtOAc–30% EtOH/EtOAc) to give the title cpd. The product was recrystallized several times from EtOH. Yield: 89 mg(46.4%). M.p. 203°–205° C. For C$_9$H$_{12}$N$_3$O$_3$F Calc.:47.2% C.; 5.3% H; Found: 46.8% C.; 5.3% H. PMR(360 MHz,d6 DMSO): 7.67(dd, 6.7 Hz, 1.5 Hz, 1, H-6), 7.19(bd, 2, NH2), 5.93(dd, 18.7 Hz, 3.5 Hz, 1, H-1'), 5.71(d, 6.7 Hz, 1, H-5), 5.21(dm,51.5, 1, H-2'), 4.94(t, 5.8 Hz, 1, OH), 4.08(m, 1, H-4'), 3.51(m, 2, H-5'), 2.6–2.4(m, 1, H-3a'), 2.12-2.198(m, 1, H-3b').

6. 2'-Deoxy-2'-fluoroarabino-5'-monomethoxytrityl-thymidine

2'-Deoxy-2'-fluoroarabino-5-methyluridine (10.4 g; 40 mM) dissolved in anhydrous pyridine (150 ml) was heated at 65–75 deg. C. for 6 hrs. with monomethoxytrityl chloride (13.9 g. 45.0 mM). The reaction mixture was poured into ice-water (1.5l) with vigorous stirring. The precipitate was filtered off, but turned oily upon standing (21.1 g; 99.0% crude). PMR(200 MHz, CDCl$_3$): 8.83(bs, 1, NH), 7.5–7.18(m, 13, aromatic and H-6), 6.84(d, 2, aromatic), 6.27(dd, 18.8 Hz, 3.2 Hz, 1, H-1'), 5.04(dm, 51.6 Hz, 1, H-2'), 4.46(dd, 20.2 Hz, 4.0 Hz, 1, H-3'), 4.01(q, 4.6 Hz, 1, H-4'), 3.80(s, 3, OCH$_3$), 3.51–3.37(m, 2, H-5'), 1.75(bs, 3, CH=CCH$_3$).

7. 2', 3'-Dideoxy-2'-fluoroarabino-thymidine

Crude 2'-deoxy-2'-fluoroarabino-5'-monomethoxytrityl-thymidine (7.0 g, 13.14 mM) was heated at 80 deg. C. for 2.5 hrs with 1,1-thiocarbonyldiimidazole (2.67 g, 15.0 mM) and the volatiles were removed in vacuo. The residue was heated to reflux in toluene (380 ml) with AIBN (120 mg), bis-tri-n-butyltin oxide (29 ml) and polymethylhydrosiloxane (29 ml). The volatiles were removed in vacuo and the residue was triturated with hexane (250 ml), cooled in dry ice, and the supernatant was discarded. The residue was purified on a silica gel column (25% EtOAc/CH$_2$CL$_2$–50% EtOAc/CH$_2$CL$_2$). The main product crystallised from CH$_2$CL$_2$-Et$_2$O to give 2',3'-dideoxy-2'-fluoroarabino-5'-(monomethoxytrityl-thymidine (2.7 g). This material was stirred for 3 hrs (45°–55° C.) in 80% aqueous acetic acid (20 ml). The volatiles were removed in vacuo and the residue was crystallized from CH$_2$CL$_2$-Et$_2$O-Hexane to give pure title compound (430 mg). This product was recrystallized with the material obtained from the silica gel column purification of the mother liquor (10% EtOH/EtOAc) to give analytically pure material (810 mg, 25.2% overall). M.p. 162°–164° C. For C$_{10}$H$_{13}$N$_2$O$_4$F Calc: 49.2% C; 5.4% H; 11.5% N. Found: 5.4% H; 11.3% N. PMR(360 MHz, d6 DMSO): 7.61(bs, 1, H-6), 5.95(dd, 16.6 Hz, 3.8 Hz, 1, H-1'), 5.26(dm, 54.9 Hz, 1, H-2'), 4.07(m, 1, H-4'), 3.62–3.48(m, 2, H-5'), 2.53–2.37(m, 1, H-3a', 2.13–1.98(m, 1, H-3b'), 1.77(bs, 3, CH=CCH$_3$).

8. 2'-Deoxy-2'-fluoroarabino-5'-monomethoxytrityl-3'-methanesulfonyl-thymidine 2'-deoxy-2'-fluoroarabino-5'-monomethoxytrityl-thymidine (10 g; 18.78 mM) in dry pyridine (65 ml) was treated dropwise at 0° C. with methanesulfonyl chloride (6 ml; 61.4 mM) and kept at 0° C. overnight. The volatiles were removed in vacuo and the residue was purified on silica gel column (25% EtOAc/CH$_2$Cl$_2$ to 45% EtOAc/CH$_2$Cl$_2$) to an oily product (7.0 g, 61%). PMR(200 MHz, CDCl$_3$): 8.40(bs, 1, NH), 7.55–7.20(m, 13, aromatic and H-6), 6.87(bd, 2, aromatic), 6.25(dd, 19.6 Hz, 3.6 Hz, 1, H-1'), 5.38(dd, 17.6 Hz, 3.4 Hz, 1, H-3'), 5.29(dd, 48 Hz, 3.6 Hz, 1, H-2'), 4.17(m, 1, H-4'), 3.81(s, 3, OCH3), 3.51(m, 2, H-5'), 3.06(s, 3, OSO$_2$CH$_3$), 1.74(bs, 3, CH=CCH$_3$)

9. 2',3'-Dideoxy-3',2-anhydro-2'-fluoroarabino-5'-monomethoxytrityl-thymidine 2'-Deoxy-2'-fluoroarabino-3'-methanesulfonyl-5'-monomethoxytrityl-thymidine (2.7 g; 4.42 mM) was dissolved in EtOH (200 ml) and heated under reflux for 2 hrs with 1N NaOH (4.6 ml). The volatiles were removed in vacuo, and the product was washed into a filtering funnel with cold water. Yield: 1.7 g(74.6%). PMR(200 MHz, CDCl$_3$):7.5–7.2(m, 12, aromatic), 6.92(s, 1, H-6), 6.80(bd, 2, aromatic), 5.37(dt, 52.0 Hz, 3.4 Hz, 1, H-2'), 5.36(m, 1, H-1, H-1'), 5.03(t, 3.2 Hz, 1, H-3'), 4.33(m, 1, H-4'), 3.77(s, 3, OCH$_3$), 3.36(bd, 2, H-5'), 1.94(bs, 3, CH=CCH$_3$).

10. 2',3'-Dideoxy-2',3'-didehydro-2'-fluoro-5'-monomethoxytrityl-thymidine

2',3'-Dideoxy-3',2-anhydro-2'-fluoroarabino-5'-monomethoxytrityl-thymidine (412 mg; 0.8 mM) and tBuOK (199.8 mg, 1.78 mM) were suspended in dry DMSO(7 ml) and stirred for 0.5 hr at room temperature under argon. The reaction mixture was poured into ice-water and acidified to pH 5.0 with 80% AcOH. The precipitate was filtered off (200 mg), but turned oily upon standing. Additional material was obtained from EtOAc extraction of the water layer. Crude product was purified on a silica gel column (45% EtOAc/Hexane–50% EtOAc/Hexane) to give pure product (190 mg, 46.1%). PMR(360 MHz, CDCl$_3$): 8.22(bs, 1, NH), 7.47(s, 1, H-6), 7.4–7.20(m, 12, aromatic), 6.92(dd, 4.5 Hz, 1.4 Hz, 1, H-3'), 6.80(m, 2, aromatic), 5.69(d, 1.3 Hz, 1, H-1'), 4.93(m, 1, H-4'), 3.77(s, 3, OCH$_3$), 3.35 (AB of ABX, 2, H-5'), 2.03(bs, 1, CH=CCH$_3$).

11. 2',3'-Dideoxy-2'3'-didehydro-2'-fluoro-thymidine

2',3'-Dideoxy-2',3'-didehydro-2'-fluoro-5'-monomethoxytrity-1-thymidine (300 mg; 0.583 mM) was stirred for 1.5 hrs at 60° C. in 80% acetic acid (5 ml) and the volatiles were removed in vacuo. The residue was purified on a silica gel column (3% EtOH in EtOAc-CH$_2$Cl$_2$ 1:1 to 5% EtOH in the same) to give the title nucleoside (40 mg; 28.3%). The product was recrystallized from CH$_2$Cl$_2$-Hexane. M.p. 129°–131° C. (decomposition). PMR(200 MHz d6 DMSO): 7.89(bs, 1, H-6), 6.75(m, 1, H-3'), 5.99(s, 1, H-1'), 5.16(t, 5.4 Hz, 1, OH), 4.80(m, 1, H-4'), 3.61(m, 2, 2, H-5'), 1.76(bs, 3, CH=CCH$_3$).

12. 2'-Deoxy-2'-fluoroarabino-3'-methanesulfonyl-5'-monomethoxytrityl-uridine The title compound was obtained from 2'-deoxy-2'-fluoroarabino-5'-monomethoxytrityl-uridine in a mesylation analogous to the mesylation of 2'-deoxy-2'-fluoroarabino-5'-monomethoxytrityl-thymidine. Yield: >99% crude. PMR(200 MHz, CDCl$_3$): 8.52(bs, 1, NH), 7.54–7.20(m, 13, aromatic and H-6), 6.84–6.89(m, 2, aromatic), 6.23 (dd, 18.4 Hz, 3.4 Hz, 1, H-1'), 5.58(dd, 8.2 Hz, 2.0 Hz, 1, H-5), 5.36(dm, 20.6 Hz, 1, H-3'), 5.30(dm, 50.6 Hz, 1, H-2'), 4.196(m, 1, H-4'), 3.81(s, 3, OCH$_3$), 3.515(bd, 2, H-5'), 3.07(s, 3, OSO$_2$CH$_3$).

13. 2',3'-Dideoxy-3', 2-anhydro-2'-fluoroarabino-5'-monomethoxytrityl-uridine.

2'-deoxy-2'-fluoroarabino-3'-methanesulfonyl-5'-monomethoxytrityl-uridine (20 g; 33.5 mM) in EtOH (400 ml) was treated with 1N NaOH(35 ml) and heated under reflux for 4 hrs. The mixture was cooled down to 5° C. and the pH adjusted to 7.5 with 80% AcOH. The precipitate was filtered off, washed with MeOH-water and dried. Yield 14.0 g (83.5%). PMR(360 MHz, d6 DMSO): 7.76 (d, 7.45 Hz, 1, H-6), 7.37–7.19(m, 12, aromatic), 6.88(d, 2, aromatic), 6.03(bd, 4.8 Hz, 1, H-1'), 5.91(dt, 50.0 Hz, 3.6 Hz, 1, H-2'), 5.89(d, 7.3 Hz, 1, H-5), 5.43(t, 2.7 Hz, 1, OH), 4.60(m, 1, H-4'), 3.72(s, 3, OCH$_3$), 3.13(m, 2, H-5').

14. 2', 3'-Dideoxy-2', 3'-dehydro-2'-fluoro-5'-monomethoxytrityl-uridine

2', 3'-dideoxy-3', 2-anhydro-2'-fluoroarabino-5'-monomethoxytrityl-uridine (4.2 g; 8.39 mM) and potassium t-butoxide (2.1 g; 18.75 mM) were stirred at r.t. in dry DMSO (120 ml) for 60 min. This mixture was poured into ice-water (600 ml) and extracted with EtOAc and dried. Yield: 4.0 g (95.2%), sufficiently pure for subsequent transformations. PMR(360 MHz, CDCl$_3$): 8.41(bs, 1, NH), 7.92(d, 8.1 Hz, 1, H-6), 7.35–7.19(m, 12, aromatic), 6.88(m, 1, H-3'), 6.83(d, 2, aromatic), 5.62(s, 1, H-1'), 5.04(d, 8.14 Hz, 1, H-5), 4.89(m, 1, H-4'), 3.43(m, 2, H-5').

15. 2',3'-dideoxy-2',3'-dehydro-2'-fluoro-5'-monomethoxytrityl-cytidine

The title compound was prepared from 2',3'-dideoxy-2',3'-dehydro-2'-fluoro-5'-monomethoxytrityl-uridine in a manner analogous to 2',3'-dideoxy-2'-fluoroarabino-5'-monomethoxytrityl-cytidine. Yield:18.8% PMR(200 MHz, d6 DMSO): 7.71(d, 7.4 Hz, 1, H-6), 7.38–7.19(m, 12, aromatic), 6.88(m, 3, aromatic and H-3'), 6.07(m, 1, H-1'), 5.37(d, 7.4 Hz, 1, H-5), 4.90(m, 1, H-4'), 3.75(s, 3, OCH3), 3.60(m, 2, H-5').

16. 2',3'-Dideoxy-2',3'-dehydro-2'-fluoro-cytidine

2'3'-Dideoxy-2',3'-dehydro-2'-fluoro-5'-monomethoxytrityl-cytidine (750 mg, 3.30 mM) was stirred in 80% AcOH (5 ml) for 5 hrs at r.t. The volatiles were removed in vacuo, and the product was purified on silica column to give 240 mg (70.4%) of the title compound. For C$_9$H$_{10}$FN$_3$O$_3$ Calc.: 47,6% C, 4.4% H, 18.5% N. Found: 47.4% C 4.4% H, 18.5% N. PMR(360 MHz, d6 DMSO): 7.85(d, 7.4 Hz, 1, H-6), 7.32(bd, 2, NH2), 6.84(bs, 1, H-3'), 5.93(s, 1, H-1'), 5.76(d, 7.4 Hz, 1, H-5), 5.05(t, 5.3 Hz, 1, OH), 4.75(m, 1, H-4'), 3.55(m, 3, H-5').

17. 2',3'-Dideoxy-2'-fluoroarabino-3'-azido-thymidine

2',3'-Dideoxy-3',2-anhydro-2'-fluoroarabino-5'-monomethoxytrityl-thymidine (850 mg; 1.65 mM) in DMF(25 ml) was stirred for 62 hrs at 105° C. with lithium azide(980 mg, 20 mM). A few crystals of potassium carbonate were added and the mixture was partitioned between water and ethyl acetate. Unreacted s.m. (140 mg) crystallized out upon trituration with ether-methylene chloride. The mother liquor (700 mg) was dissolved in 80% AcOH (5 ml) and stirred for 6 hrs at 35 deg. C. Crude product was purified on a silica gel column (50% EtOAc in CH$_2$Cl$_2$) to give the title cpd (150 mg, 31.9% overall). For C$_{10}$H$_{12}$N$_5$O$_4$F Calc.:42.1% C, 4.2% H. Found: 42.3% C, 4.1% H. PMR(360 MHz, DMSOd6): 11.46(bs, 1, NH), 7.60(s, 1, H-6), 6.14(dd, 10.9 Hz, 5.4 Hz, 1, H-1'), 5.37(dt, 54.0 Hz, 5.4 Hz, 1, H-2'), 5.34(bs, 1, OH), 4.51(ddd, 22.4 Hz, 7.5 Hz, 5.3 Hz, 1, H-3'), 3.82(m, 1, H-4'), 3.68(m, 2, H-5'), 1.77(bs, 3, CH=CCH$_3$).

18. 2',3'-Dideoxy-2'-fluoroarabino-5'-monomethoxytrityl-uridine through hydrogenation of 2',3'-dideoxy-2',3'-dehydro-2'-fluoro-5'-monomethoxytrityl-uridine 2',3'-Dideoxy-2',3'-didehydro-2'-fluoro-5'-monomethoxytrity-1-uridine (450 mg, 0.9 mM) was hydrogenated over 10% Pd/C (85 mg) in ethanol (60 ml) solution for 2 hrs. Filtration and evaporation of the solvent in vacuo yielded the crude product, which was subsequently purified on a silica gel column (15% EtOAc in CH$_2$Cl$_2$ to 25% EtOAc in CH$_2$Cl$_2$). Yield: 300 mg (66.4%) MS(EI): M+502. This compound is identical to the one obtained through the deoxygenation route, described before.

What is claimed is:

1. A process for producing a compound having the formula

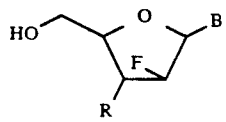

wherein
B is derived from a member selected from the group of bases consisting of purine, aza-purine, deaza-purine, pyrimidine, aza-pyrimidine, deaza-pyrimidine, and triazole ring bases, with the proviso that B is not adenine, and
R is hydrogen, comprising the steps of:
(a) reacting the corresponding 2'-deoxy-2'fluoroarabino-nucleoside with a hydroxy-protecting group reagent to selectively protect the 4'-hydroxymethyl group;
(b) subjecting the intermediate from step (a) to reductive deoxygenation to convert the 3'-hydroxy group in the intermediate from step (a) to a 3'-hydrogen group; and
(c) deprotecting the 4'-hydroxymethyl group.

2. The process for producing a compound according to claim 1 wherein B is a pyrimidine base.

3. A process for producing a compound having the formula

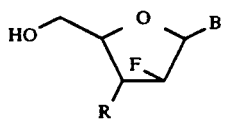

wherein
B is derived from a member selected from the group of bases consisting of purine, aza-purine, deaza-purine, pyrimidine, aza-pyrimidine, deaza-pyrimidine, and triazole ring bases, with the proviso that B is not adenine, and
R is hydrogen, comprising the steps of:

(a) reacting the corresponding 2'-deoxy-2'fluoroarabino-nucleoside with a hydroxy-protecting group reagent to selectively protect the 4'-hydroxymethyl group;

(b) subjecting the intermediate from step (a) to reaction conditions effective to convert the 3'-hydroxy group to 3'-O-leaving group substituent;

(c) subjecting the intermediate from step (c) to elimination reaction conditions to form a double bond between the 2'- and 3'-positions of the 5-membered ring system;

(d) deprotecting the 4'-hydroxymethyl group; and (e) subjecting the intermediate from step (d) to reducing conditions effective to reduce the double bond connecting the 2' and 3' carbon atoms of the 5-membered ring system.

4. A process for producing a compound having the formula

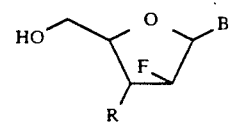

wherein B is selected from the group consisting of uracil, thymine, 5-ethyluracil, cytosine, 5-vinyluracil, halovinyluracil, 5-halovinyluracil, 5-haloethyluracil, said halovinyl, halomethyl and haloethyl groups containing from 1 to 4 F, Cl or Br atoms and wherein R is selected from the group consisting of $-N_3$, $-CN$, $-NHCN$, $-F$, $-Cl$, $-Br$, $-NH_2$, $-NHR'$, $-NR'R'$, $-SR'$, $-S(=O)-R'$ and $-S(=O)_2R'$ groups wherein each R' is independently selected from $C_1-C_3$ alkyl, phenyl, and tolyl groups, comprising the steps of (a) subjecting the corresponding 2'-deoxy-2'-fluoroarabino-nucleoside having a hydroxy protecting group at the 5'-position and a 3'-O-leaving group to conditions effective to from a 3',2-anhydro bond; and (b) reacting the intermediate from step (a) with a nucleophile corresponding to substituent R to disrupt the 3', 2-anhydro bond and to introduce R as the 3'-substituent.

* * * * *